(12) United States Patent
Bischoff (10) Patent No.: US 12,308,098 B1
(45) Date of Patent: May 20, 2025

(54) PERSONAL AND REUSABLE INFECTION STATUS PASSPORT DEVICE THAT IS CONFIGURED TO TEST FOR COVID-19 AND INFECTIOUS DISEASE

(71) Applicant: Walter George Bischoff, Henderson, NV (US)

(72) Inventor: Walter George Bischoff, Henderson, NV (US)

( * ) Notice: Subject to any disclaimer, the term of this patent is extended or adjusted under 35 U.S.C. 154(b) by 0 days.

(21) Appl. No.: 18/077,918

(22) Filed: Dec. 8, 2022

Related U.S. Application Data (60) Provisional application No. 63/288,424, filed on Dec. 10, 2021.

(51) Int. Cl.
  *G16H 10/65* (2018.01)
  *G16H 30/40* (2018.01)
  *G16H 50/80* (2018.01)

(52) U.S. Cl.
  CPC ............ *G16H 10/65* (2018.01); *G16H 30/40* (2018.01); *G16H 50/80* (2018.01)

(58) Field of Classification Search
  CPC ......... G16H 10/65; G16H 50/80; G16H 30/40
  See application file for complete search history.

(56) References Cited

U.S. PATENT DOCUMENTS

| 2013/0203043 A1* | 8/2013 | Ozcan ................. G01N 21/645 435/7.1 |
| 2018/0156734 A1* | 6/2018 | Blanch ................. G01J 3/0208 |
| 2020/0124587 A1* | 4/2020 | Dechev ............... G01N 33/493 |
| 2020/0155045 A1* | 5/2020 | Sharrock ............ A61B 5/14507 |
| 2020/0383664 A1* | 12/2020 | Loudermilk ....... A61B 10/0051 |

OTHER PUBLICATIONS

BD Veritor™ System For Rapid Detection of SARS-COV-2. Cardinal Health. Mar. 2021, https://www.cardinalhealth.com/content/dam/corp/web/documents/ifu/cardinal-health-eua-bd-veritor-ifu.pdf (Year: 2021).*

* cited by examiner

*Primary Examiner* — Gregory D. Moseley
(74) *Attorney, Agent, or Firm* — Bold IP PLLC; Houda El-Jarrah (57) ABSTRACT

A personal and reusable infection status passport device is disclosed that is configured to test for Covid-19 and infectious disease using photo and color analysis. The personal and reusable infection status passport device provides a supervisory testing unit/system to ensure testing is current and accurate. The quick and ease of use will allow for frequent testing so the individual will know their status without spending hours at a clinic or large sums of money on many single use tests. The test units are easier to produce and use with the main device. The device is capable of using a time stamp to ensure the test is current. The included processor and software will create a "status passport" system that will allow users to share their Covid-19 status as needed to comply with state, federal, local, and OSHA.

15 Claims, 6 Drawing Sheets

PERSONAL AND REUSABLE INFECTION STATUS PASSPORT DEVICE THAT IS CONFIGURED TO TEST FOR COVID-19 AND INFECTIOUS DISEASE

CLAIM OF BENEFIT TO PRIOR APPLICATION

This application claims benefit to U.S. Provisional Patent Application 63/288,424, entitled "A PERSONAL AND REUSABLE INFECTION STATUS PASSPORT DEVICE THAT IS CONFIGURED TO TEST FOR COVID-19 AND INFECTIOUS DISEASE," filed Dec. 10, 2021. The U.S. Provisional Patent Application 63/288,424 is incorporated herein by reference.

BACKGROUND

The spread of Covid-19 regularly occurs due to, in part, a lack of access to affordable and readily available testing. Also, there is no system available for validating Covid-19 status that can act as a "Passport" for infection status along with a digital app or display screen.

Current tests are single use and have no personalization. The single use makes testing costly and limits inventory of entire units. At a clinic it can take days to be seen for a test and receive results. The devices also can be manipulated to provide false results as there is no supervisory system in place. There is also no timestamp for test verification.

Therefore, what is needed is a quick, inexpensive, and easy to use testing device that will allow for frequent testing of infectious disease which also indicates a disease status for a tested individual and acts as a virtual infectious status passport, thereby allowing individuals to show their Covid-19 or other infectious disease status upon request, with a mechanism to ensure that test results and timestamp cannot be falsified.

BRIEF DESCRIPTION

Some embodiments of the invention include a novel personal and reusable infection status passport device that is configured to test for Covid-19 and infectious disease using photo and color analysis and available test cartridges. In some embodiments, the personal and reusable infection status passport device uses test strips that are easy to produce and can be refilled in interchangeable trays that are configured to insert into a tray insert slot of the personal and reusable infection status passport device.

In some embodiments, the personal and reusable infection status passport device comprises (i) an imaging module, (ii) a light source, (iii) a scanner monitor, (iv) a printed circuit board (PCB), (v) an on-board processor with a clock, (v) a power source, (vi) a housing that encapsulates the light source, the scanner monitor, the PCB, the processor, and the power source, and (vii) a tray insert slot cut out from the housing and configured to receive test strips on interchangeable trays for testing.

In some embodiments, the imaging module comprises a photoelectric sensor. In some embodiments, the photoelectric sensor comprises a photoelectric resistor. In some embodiments, the light that penetrates through (or is reflected back from) the test strip on the interchangeable tray is detected by the photoelectric resistor which outputs the detected light intensity as a wavelength measurement to the processor.

In some embodiments, the scanner monitor is communicably connected to the on-board processor of the PCB. In some embodiments, the scanner monitor is configured to detect prior negative tests. In some embodiments, the scanner monitor performs a supervisory check so results cannot be falsified with a previously negative test. When a test strip from a prior negative test is used, the scanner monitor sends a notification to the on-board processor that the test is invalid. In some embodiments, the scanner monitor receives timing data from the processor and determines whether the test strip on the interchangeable tray is inserted for a testing time duration required for testing. In some embodiments, the scanner monitor invalidates tests that do not satisfy the testing time duration.

In some embodiments, the PCB comprises a single board computer. In some embodiments, the PCB comprises a single board computer, such as, but not limited to, an Arduino or Raspberry Pi. In some embodiments, the single board computer comprises a wireless communication transceiver and onboard antenna. In some embodiments, the wireless communication transceiver comprises a Bluetooth module. In some embodiments, the wireless communication transceiver comprises a WiFi module. In some embodiments, the on-board processor (with the clock) is an assembled component of the PCB.

In some embodiments, the power source comprises a battery. In some embodiments, the battery comprises a rechargeable battery. In some embodiments, the battery comprises a plurality of batteries.

In some embodiments, the personal and reusable infection status passport device further comprises a computer connection, an Internet connection, and a graphics processing unit.

In some embodiments, the graphics processing unit is configured to convert test results to graphical data that is output to a personal electronics device such as, but not limited to, a computer or phone over the wired or wireless connection. In some embodiments, the onboard computer connection comprises a wired connection to an external computer that is configured to run image processing software. In some embodiments, the computer connection comprises a wireless connection to the external computer and a mobile device is configured to run a mobile app.

In some embodiments, the wired connection is supported by an Ethernet connection between the computer and the personal and reusable infection status passport device. In some embodiments, the personal and reusable infection status passport device further comprises a wired or wireless connection to the Internet. In some embodiments, the wired connection is supported by an Ethernet connection between the personal and reusable infection status passport device and a gateway router that is connected to the Internet. In some embodiments, the wireless connection to the Internet comprises a WiFi connection to a wireless router that is connected to the Internet. In some embodiments, the wireless connection from the personal and reusable infection status passport device to the computer or a mobile device comprises a Bluetooth connection.

In some embodiments, the personal and reusable infection status passport device also comprises a display that visually outputs Covid-19, or other infectious disease, status of a user. In some embodiments the user will use a personal electronics or mobile device (phone) application display that visually outputs Covid-19, or other infectious disease, status of a user.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications. Also, all dimensions specified in this disclosure are by way of example only and are not intended to be limiting. Furthermore, the proportions shown in these Figures are not necessarily to scale. As will be understood by those of ordinary skill in the relevant art, the actual dimensions and proportions of any system, any device or part of a system or device disclosed in this specification will be determined by its intended use.

Devices that implement the various features of the invention will be described with reference to the drawings. The drawings and the associated descriptions are provided below to illustrate embodiments of the invention and not to limit the scope of the invention. Reference in the specification to "one embodiment", "an embodiment", or "some embodiments" is intended to indicate that a particular feature, structure, or characteristic described in connection with the embodiment or embodiments is included in at least one embodiment, and possibly multiple embodiments, of the invention. The appearances of the phrases "in one embodiment", "an embodiment", or "some embodiments" in various places in the specification are not necessarily all referring to the same embodiment.

Throughout the drawings, reference numbers are re-used to indicate correspondence between referenced elements.

As used in this disclosure, except where the context requires otherwise, the term "comprise" and variations of the term, such as "comprising", "comprises", and "comprised" are not intended to exclude other additives, components, integers, or steps.

Embodiments of the invention described herein are directed to a personal and reusable infection status passport device that is configured to test for Covid-19 and infectious disease using image and color analysis. In some embodiments, the personal and reusable infection status passport device uses test strips that are easy to produce and can be refilled in interchangeable trays that are configured to insert into a tray insert slot of the personal and reusable infection status passport device.

In some embodiments, the personal and reusable infection status passport device comprises (i) an imaging module, (ii) a light source, (iii) a scanner monitor, (iv) a printed circuit board (PCB), (v) an on-board processor with a clock, (v) a power source, (vi) a housing that encapsulates the light source, the scanner monitor, the PCB, the processor, and the power source, and (vii) a tray insert slot cut out from the housing and configured to receive test strips on interchangeable trays for testing.

In some embodiments, the imaging module comprises a photoelectric sensor. In some embodiments, the photoelectric sensor comprises a photoelectric resistor. In some embodiments, the light that penetrates through (or is reflected back from) the test strip on the interchangeable tray is detected by the photoelectric resistor which outputs the detected light intensity as a wavelength measurement to the processor. In some embodiments, an image capture device is used to capture and monitor the test and onboard software analyzes the test and produces a result.

In some embodiments, the scanner monitor is communicably connected to the on-board processor of the PCB. In some embodiments, the scanner monitor is configured to detect prior negative tests. In some embodiments, the scanner monitor performs a supervisory check so results cannot be falsified with a previously negative test. When a test strip from a prior negative test is used, the scanner monitor sends a notification to the on-board processor that the test is invalid. In some embodiments, the scanner monitor receives timing data from the processor and determines whether the test strip on the interchangeable tray is inserted for a testing time duration required for testing. In some embodiments, the scanner monitor invalidates tests that do not satisfy the testing time duration.

In some embodiments, the PCB comprises a single board computer. In some embodiments, the PCB comprises an Arduino single board computer. In some embodiments, the single board computer comprises a wireless communication transceiver and antenna. In some embodiments, the wireless communication transceiver comprises a Bluetooth module. In some embodiments, the wireless communication transceiver comprises a WiFi module. In some embodiments, the on-board processor (with the clock) is an assembled component of the PCB.

In some embodiments, the power source comprises a battery. In some embodiments, the battery comprises a rechargeable battery. In some embodiments, the battery comprises a plurality of batteries.

In some embodiments, the personal and reusable infection status passport device further comprises a computer connection, an Internet connection, and an onboard or external graphics processing unit.

In some embodiments, the graphics processing unit is configured to convert test results to graphical data that is output to a computer over the computer connection. In some embodiments, the computer connection comprises a wired connection to an external computer that is configured to run image processing software. In some embodiments, the computer connection comprises a wireless connection to the external computer and a mobile device is configured to run a mobile app.

In some embodiments, the wired connection is supported by an Ethernet connection between the computer and the personal and reusable infection status passport device. In some embodiments, the personal and reusable infection status passport device further comprises a wired or wireless connection to the Internet. In some embodiments, the wired connection is supported by an Ethernet connection between the personal and reusable infection status passport device and a gateway router that is connected to the Internet. In some embodiments, the wireless connection to the Internet comprises a WiFi connection to a wireless router that is connected to the Internet. In some embodiments, the wireless connection from the personal and reusable infection status passport device to the computer or a mobile device comprises a Bluetooth connection.

In some embodiments, the personal and reusable infection status passport device also comprises a display that visually outputs Covid-19 status of a user. The personal electronics device app will also display the Covid-19 (and other infectious disease) status of a user.

As stated above, the spread of Covid-19 regularly occurs due to, in part, a lack of access to affordable and readily available testing. The single use makes testing costly and limits inventory of entire units. At a clinic it can take days to be seen for a test and receive results. The devices also can be manipulated to provide false results as there is no supervisory system in place including timestamps.

Also, there is no system available for validating Covid-19 status that can act as a "Passport" for infection status. The personal and reusable infection status passport device that is configured to test for Covid-19 and infectious disease using photo and color analysis described in the present disclosure solves these problems. In particular, the personal and reusable infection status passport device is a user-specific device that utilizes existing methods for Covid-19 testing and also acts as a supervisory system and a passport indicating the user's Covid-19 status. The personal and reusable infection status passport device is built for ease of use that enables frequent (e.g., daily or more frequent) testing. By testing frequently with a validation method, a user of the personal and reusable infection status passport device can quickly determine their present Covid-19 infectious status. When a user knows their present Covid-19 status, they can begin to isolate before spreading the disease and public venues can function with reduced risk of disease transmission.

Additionally, the personal and reusable infection status passport device is reusable and portable. Combined with the ease of use and quick turnaround time for obtaining the test results, the personal and reusable infection status passport device can be used frequently to test and obtain their Covid-19 status so that users can engage in routine activities in close proximity to others with the knowledge and peace of mind that their Covid-19 status is as accurate as the most recent test results indicate. In this way, a user need not wonder and worry as much about their Covid-19 status and about infecting others. Also public venues could function without concerns of disease transmission and could relax certain precautions, such as distancing and masking.

Furthermore, for situations and events in which Covid-19 restrictions are present, the personal and reusable infection status passport device acts as a veritable "passport" system that effectively satisfies requirements from authoritative bodies, such as, without limitation, OSHA, Federal, state, and local testing requirements.

Embodiments of the personal and reusable infection status passport device that is configured to test for Covid-19 and infectious disease using photo and color analysis described in this specification differ from and improve upon currently existing options. In particular, some embodiments differ from current Covid-19 testing options, which are time-consuming, expensive, and typically require a lab analysis that necessitates a time and distance issue from the time and place a Covid-19 test is taken by a user to the time and place a lab gets the biosample to test for Covid-19 to the time and place of delivery of the Covid-19 test results back to the user. Additionally, there is no status passport system currently in place by the conventional testing mechanisms.

By contrast, the personal and reusable infection status passport device described in this specification includes a main device that is reusable and which is configured to allow users to test frequently and obtain validated test results quickly to provide Covid-19 status updates. In addition, the personal and reusable infection status passport device create a Covid-19 passport system that allows the user to reveal their present Covid-19 status to others with timestamp indicators of the Covid-19 tests/results and a supervisory system to prevent status manipulation and validate the user's test results. Specifically, the personal and reusable infection status passport device will have an onboard system that will monitor the reaction of the user's bio-sample and a testing medium to ensure a user is not trying to subvert the system by simply using a previously negative test, blank test, or swap tests while waiting for the results.

In addition, the personal and reusable infection status passport device uses any manufacturer's test medium which is easier and cheaper to make and will allow significantly less cost per test. The high costs of conventional Covid-19 testing mechanisms has the effect of discouraging users from performing frequent testing until or unless they experience symptoms. Lack of access is also a deterrent for many users since going to a clinic takes time and can be costly. Furthermore, some users may be deterred by the possibility of catching/spreading disease while waiting in a clinic or testing facility for a test to be performed or for lab results to be run. The personal and reusable infection status passport device, however, provides quick validated testing and results in an easy-to-use device that utilizes inexpensive test strips, thereby allowing for frequent testing so the individual will know their status without spending hours at a clinic or large sums of money on other validation mechanisms and tests.

The personal and reusable infection status passport device that is configured to test for Covid-19 and infectious disease using photo and color analysis of the present disclosure may be comprised of the following elements. This list of possible constituent elements is intended to be exemplary only and it is not intended that this list be used to limit the personal and reusable infection status passport device of the present application to just these elements. Persons having ordinary skill in the art relevant to the present disclosure may understand there to be equivalent elements that may be substituted within the present disclosure without changing the essential function or operation of the personal and reusable infection status passport device.

1. The device is designed to be small in size, such that the device is easily capable of being transported and kept on one's person. The device can be made from any material suitable for this application. The device houses several components including, without limitation, mounting brackets, slots, swivels, mixtures, primers, testing units, computers, image capture devices/scanners, processors, interfaces, batteries, a start button, etc.
2. The device (#1) utilizes an interchangeable tray which is inserted into a tray insert slot of the device. The interchangeable tray can also serve as a seal to prevent moisture or dust intrusion. The mechanism in which the interchangeable tray closes or locks into place is subject to change (seal, rotation, clasp, etc.).
3. The interchangeable tray (#2) houses the sample test unit (or test strip). A used sample test unit can be removed and a new sample test unit/strip can be installed. Each sample test unit is capable of receiving a sample (or "biosample) of human bodily fluid including, without limitation, saliva, nasal fluids, urine, blood, etc. The shape, material, and orientation is subject to change.
4. The sample units/test strips (#3) include chambers for activation solutions, catalysts, and collection channels. Each sample test unit (#3) includes a discrete attached sample chamber for human bodily fluid sample collection. The design may include channels to optimize the reaction between the solution and sample. Analysis is possible when a reaction occurs between the solution, test medium, and user sample. The strips can include any 3rd party manufacturer's test mediums.
5. The sample test unit (#3) is also capable of mixing any of the activation solutions and the user's collected specimen by any means. The mixture is initiated by the device removing discrete boundaries via the structure of the unit and device (#1, #2, and #3).
6. The sample test unit (#3) is equipped to perform fluorophore testing or other testing. To do so, a light source for sample activation is installed.
7. The device (#1) is equipped with, but not limited to, a photosensor, scanner, imager, camera, etc., to detect and monitor the test (#3) sample for results associated with the respective infectious disease, virus, or other test. The photosensor, camera and scanner outputs to a processor (next item) for analysis.
8. The device (#1) includes an on-board processor that is configured to receive signal input from the photosensor, camera, and scanner (#7). The processor then analyzes the input to determine the results of the user's test. The processor also includes an onboard clock to supervise the reaction (noted in #3-7 above) to ensure a full test is being performed and time stamped at the time of completion. This serves as the validation method as the user cannot use a pre-used, blank, or swapped test.
9. The device (#1) may be equipped with an (optional) display (screen). When so equipped, the display screen may provide visual output of a user interface (UI) with virtual interface buttons for interacting with the UI. Alternately, the device (#1) can be equipped with physical (tangible) interface buttons that are communicably connected to the UI and serve to affect user selections within the UI displayed on the screen. Furthermore, the display screen of some embodiments functions by the input from the processor (#8). In particular, the display screen visually outputs results and time stamps. The display screen also shows an indication of the user's positive or negative test status, or error/out of range status.
10. The processor and interface (#8 and #9) are capable of remote connectivity, but the device (#1) does not require remote connectivity to work. The connectivity allows for interface with an external computing device such as, without limitation, a mobile device, a PC, a laptop, etc.
11. When connectivity (#10) is utilized, software ensures the interface between the device (#1), processor (#8), and visual display (#9). The software also provides several additional functions including, without limitation, configuration of the device, review of results, review of past results, adding a new test medium etc.
12. The software or "app" (#11) is configured to function as a status passport with the ability and option to upload and/or interface with state or federal platforms regarding individual Covid-19 status for jurisdictional requirements including, without limitation, OSHA workplace requirements. The app will display the time from the previously negative test and count up by the second. The screen will change colors over a predetermined period of time for ease of viewing. The app will also allow the user to start the test, display previous results, and communicate with the manufacturer. The app will have a login that can only be used by one person and will have to be configured for the new user's credentials (e.g., Username, Password, etc.) and other optional information.
13. The device (#1) includes an on-board battery with the ability to be charged or changed.
14. All the components configuration and material are subject to change. Items may be affixed to the main device with the ability to be removed and reattached. This will allow for improved testing, cleaning, and repair.

The various elements of the personal and reusable infection status passport device that is configured to test for Covid-19 and infectious disease using photo and color analysis of the present disclosure may be related in the following exemplary fashion. It is not intended to limit the scope or nature of the relationships between the various elements and the following examples are presented as illustrative examples only.

The main device (#1) houses all the other components and functions (#2-9 and optionally #10). The device will have an on-board battery (#13). These components can be removed as needed to perform testing. The interchangeable tray (#2) can be removed from the device (#1) and will house a single sample test unit (#3). Upon completing a test, the user removes the interchangeable tray (#2) from the device (#1) and then removes the sample test unit (#3) from the interchangeable tray (#2). The user may then insert a new sample test unit (#3) into the interchangeable tray (#2) and then insert the interchangeable tray (#2) back into the main device (#1). When this is done, the main device (#1) is ready for testing.

To perform testing the user obtains a bodily fluid sample using any of several well-known methods including, without limitation, a swabbing item. The user then applies the sample to the sample test unit (#3). The user adds a solution for the testing medium, membranes, and testing channels (#4-5). When inserting the prepared sample unit (#3 with bodily fluid sample), mixing will occur at this time or when the sample unit on the interchangeable tray (#2) is inserted into the tray insert slot of the main device (#1). The interchangeable tray (#2) is inserted into the tray slot with the prepared sample test unit (#3) onboard and then back into the main device (#1).

The main device (#1) may (optionally) have a physical 'start button' to initiate a test. However, normally, the user will use the software app (#12) to start the test. The test process utilizes an internal controlled light source (#6), the photosensor, camera, and scanner (#7), and the processor/analysis (#8). The light source (#6) allows the photosensor, camera, and scanner analyzer (#7) to record the emission from the sample test unit (#3). Based on the observed results, the processor (#8) determines whether the user's sample is normal, positive (infected), or "abnormal" (which prevents users from subverting the test). The processor (#8) monitors the test and ensures that an already negative or blank test has not been inserted. The processor (#8) ensures the test has not been started and swapped out for a pre-used test. The processor (#8) monitors for the normal test duration and provides a time stamp.

The main device (#1) may also be equipped with a visual display (optional) and interface buttons (optional) (#9) on the front panel of the main device (#1). The interface (optional) (#9) visually outputs various device statuses, test results, configuration interfacing, time stamps of results, passport interfacing, and other indications on the display screen (optional) (#9) as required. The software app (#12) is the preferred method of operation and can perform all the functions of (#9). The on-board processor (#8) is capable of remote (via wireless protocols, such as Bluetooth) or hardwired connectivity (#10) to a mobile device, laptop, PC, or any other computing device with remote connectivity. When using the on-board processor's (#8) remote interface, software, such as a mobile "app" (#12), or other software application (#12) is available for download to the user's personal device. When enabled by the user, the "app" software (#12) is able to perform interface and connections for the jurisdictional entities (#12). It should be noted that the app (#12) is the preferred method for operations.

The processor (#8) will scan the test strip (#3) and determine if a (manufacturer dependent) wavelength light change has occurred and the occurrences. The photosensor, camera, image scanner (#7) will capture the image and light data emitting from the test strip (#3) and export it to the processor (#8). The processor (#8) will analyze the data from test strip (#3) and determine the results based on the present data. For instance, if a single red line indicates a negative test and two red lines indicates a positive test, then when the processor (#8) detects two red lines, a positive results is returned. In contrast, when the processor (#8) detects only a single red line, then a negative test is returned. Rounding out the possibilities, when or if no red lines are detected after a predetermined time duration (in some embodiments, the predetermined time duration is fifteen minutes), then an error is returned. The error may state a status, such as "blank test" or similar message indicative of a problematic test. Similarly, if one or two red lines are immediately detected (that is, at time zero '0'), then an error is returned based on a pre-used test. The time of the testing will be timestamped. This acts as the validation method as it prevents tampering or subverting the testing.

The personal and reusable infection status passport device that is configured to test for Covid-19 and infectious disease using photo and color analysis of the present disclosure generally works by a user obtaining a new sample test unit (#3). The user then utilizes a swabbing item (or other acceptable item) to obtain a bodily fluid sample. The biosample is then placed into the sample test unit (#3) and the activation solution (#4) is introduced to the biosample. In some embodiments, the sample test unit (#3) or test strip is pre-coated with an antigen, or other reaction agent, and will (or will not) react with the user's sample. This reaction (or lack of reaction) occurs at the analysis section with capture points for test analysis. At this stage, the light source (#6). The sample image and light signal is captured by the photosensor, camera, and scanner (#7) to analyze test for various wavelengths of color and occurrences of the light. The wavelength values are interpreted by the processor (#8) to determine whether a positive or negative test is present. The processor (#8) also includes logic to reject a pre-used test strip. That is, if the user inserts a previously used test strip (from a prior test), the processor (#8) returns an "error" code.

When the test is valid and completed, the processor (#8) returns a time stamp and the user's status. The processor (#8) uses baseline data and runs the current test values through a logic chain.

When the values are excessive or concluded too quickly, tray (#2) is removed, or no wavelength changes are detected, the device (#1) yields an error (e.g., no sample, contaminated, etc.). A normal value compared to the baseline and other researched values registers a "covid negative" result. If the values are outside the normal range, and close to researched Covid positive values, the device will indicate a "covid positive" result.

The results of this test may be displayed on the display screen (#9) of the main device (#1). The results include visual output of a timestamp for the test. If enabled, the processor's Bluetooth function (or other wireless function) or hardwired connectivity uploads the results to the user's devices (mobile phone, laptop, PC, etc.). The data can also be uploaded to other databases via the app and internet connectivity. The software app (#12) is capable of starting a test, displaying results, status of the test, and results of the test. The software app (#12) will also have a display screen with an upward time counter showing the duration (days, hours, minutes, seconds) since the previously negative test. This screen will also include a specific color to provide easier identification of a proximate interval. The software app will be stored on the user's personal electronic device. The app will be configured to include user credentials (such as username and (encrypted) password) and other optional information. The app will be tethered to the main device and processor (#1 and #8) such that only a single user can access the main device and testing abilities at any given moment. The app will act as a means to update the main device using an internet connection and a wired/wireless connection.

To make the personal and reusable infection status passport device that is configured to test for Covid-19 and infectious disease using photo and color analysis of the present disclosure, a person would assemble the main device (#1) as a housing or a shell of generic materials, likely a metallic, plastic, or other polymer material which then encapsulates/houses all the components. The shape and size may vary provided it can house the components noted above.

The main device (#1) would be provided with a slot for inserting interchangeable trays (#2) of similar or same material(s) as the device (#1) such that the interchangeable tray (#2) inserts into the tray slot of the device (e.g., by sliding into place, snapping into place when inserted, or by a threaded twist for interchangeable trays of a circular design, or by a latching operation, etc.) and forms a cover to protect the internal components. The interchangeable tray (#2) would be made to hold the sample test unit (#3) steady and not interfere with the testing. The shape, size, and configuration may vary, but the person would need to insert the interchangeable tray (#2) within the device (#1) that houses the sample test unit (#3) in a relatively secure/steady manner. On the other hand, the person may design the sample test unit (#3) in a way that may or may not house the solutions/mixing (#4) and channels/capture points (#5). However, the person would ensure that the unit is transparent and capable of allowing a light source (#6) to illuminate and pass light through to the photosensor (#7). The person would make the sample test unit (#3) in a way to easily fit into the respective interchangeable tray (#2) and have a port to introduce a bodily fluid sample. The sample test unit (#3) will also have the activating solution pre-filled or introduced. The person would prepare each sample test unit (#3) with special orientation considerations such as channels or capture points, as needed. The sample test units (#3) would be made to seal in order to prevent internal contamination of the main device (#1). The shape, size, and orientation of these sample units (#3) may vary so long as it is capable of performing the functions listed above and fits within the interchangeable tray (#2). The material used to make the sample test unit (#3) may vary provided it can support the testing process. However, the sample test unit (#3) medium must be precoated with an antigen (e.g., SARS antigen) to produce a reaction that will be analyzed.

The photosensor, camera, and scanner (#7) would be of the sort that is configured to receive images and light energy and convert the detected data into a digital color signal to be received by the processor (#8). The processor (#8) would be configured to record duration to ensure the test was unaltered when inserted, and when valid, capable of determining a positive, negative, or out of range (or other error) result. The processor (#8) would also be configured to generate and provide a time stamp of each tested result. The photosensor, camera, and scanner (#7) would be affixed to the internals of the main device (#1) and powered by the battery (#13). The photosensor, camera, and scanner (#7) and the battery (#13) should be affixed in an orientation that admits light to illuminate the sample test unit (#3) and be able to receive the light signal at the photosensor, camera, and scanner (#7). However, in some embodiments, a light source (#6) and the photosensor (#7) can be disposed on or equipped within the sample test unit (#3) if isolation and external light pass-through cannot be achieved.

The processor (#8) is mounted in the main device (#1) and connected to the display screen and interface (#9), which itself will be designed to receive input from the processor (#8) to output for visual display. The medium of the display (screen) may vary, but shall be capable of displaying letters, numbers, and basic symbols. Typical display screens include, without limitation, LED and OLED displays, but the size and configuration are inconsequential.

To use the personal and reusable infection status passport device that is configured to test for Covid-19 and infectious disease using photo and color analysis of the present disclosure, a person (or "user") will obtain a new sample test unit with pre-filled testing solution. The user will obtain a bodily fluid sample and place the biosample in the sample test unit. The user will then introduce the fluid activation solution to the biosample. The user would then place the prepared sample test unit inside the interchangeable tray and insert the interchangeable tray into the tray insert slot of the main device to seal. The user then starts the test process by pressing the buttons on the user interface (e.g., the "start button" or mobile app start tool running on a mobile device if remote connectivity is enabled). The test process is automated from this time.

Upon completion the device displays results on the visual display and possible external displays (e.g., the user's connected device). Upon completion the user will remove the interchangeable tray and discard the used sample test unit, which is followed by the user inserting the interchangeable tray back into the device to act as a dust guard and prevent contamination. The user will configure the software and main device to upload the results to their connected devices and any "passport" databases of their choice. The user can also use the results and time stamp as proof of negative test results as necessary. General assembly and configuration of the device is subject to change and should allow for internal access for cleaning and troubleshooting if required.

Figure 1:
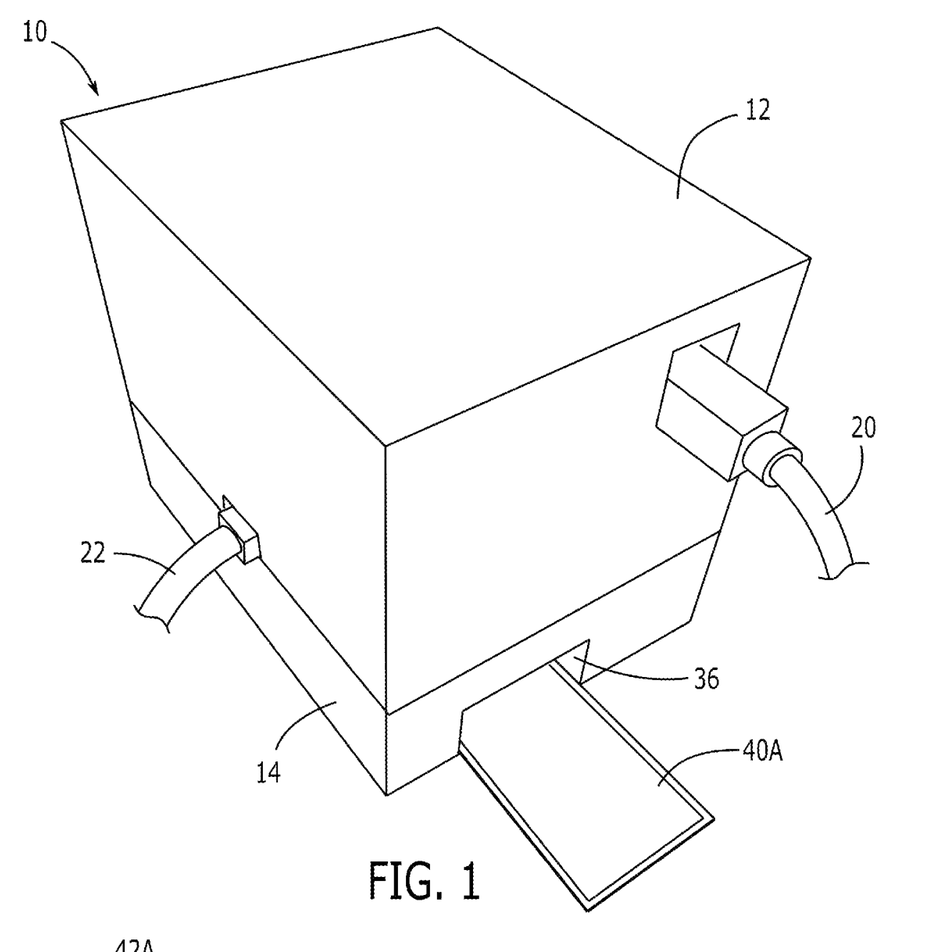
FIG. 1 conceptually illustrates a front perspective view of a personal and reusable infection status passport device in some embodiments that tests for Covid-19, tracks status, and monitors tests, while the device is in use.

By way of example, FIG. 1 conceptually illustrates a front perspective view of a personal and reusable infection status passport device 10 that tests for Covid-19, tracks status, and monitors tests, while the device is in use. As shown in this figure, the personal and reusable infection status passport device 10 comprises a top housing enclosure 12, a bottom housing enclosure 14, a computer connection 20, an Internet connection 22, and a tray insert slot 36. The tray insert slot 36 is configured to receive insertion of an interchangeable tray 40A.

Figure 2:
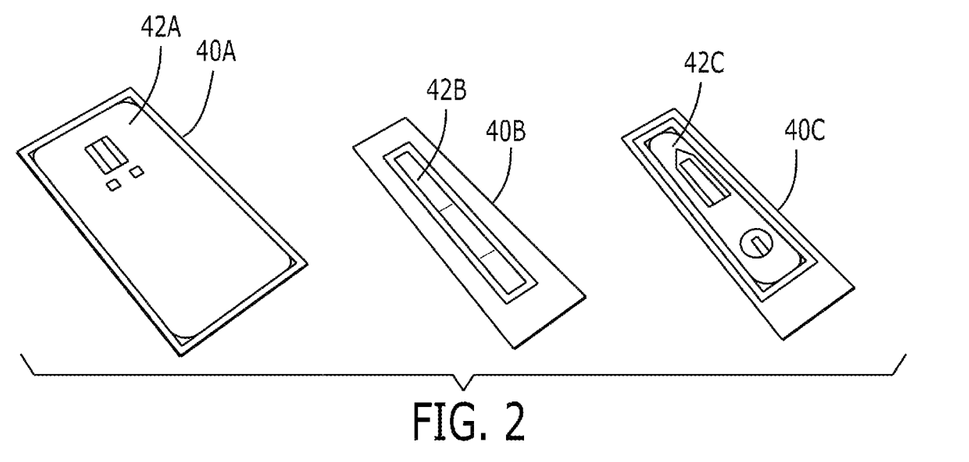
FIG. 2 conceptually illustrates a perspective view of exemplary test strips used to test for Covid-19 in the personal and reusable infection status passport device.

Now turning to FIG. 2, several exemplary test strips used to test for Covid-19 in the personal and reusable infection status passport device 10 are shown. Specifically, a plurality of interchangeable trays 40A, 40B, and 40C are shown with a plurality of different types of test strips 42A, 42B, and 42C, respectively. The interchangeable trays 40A, 40B, and 40C are configured to insert into the tray insert slot 36 so that the personal and reusable infection status passport device 10 can test the test strips 42A, 42B, and 42C for Covid-19.

Figure 3:
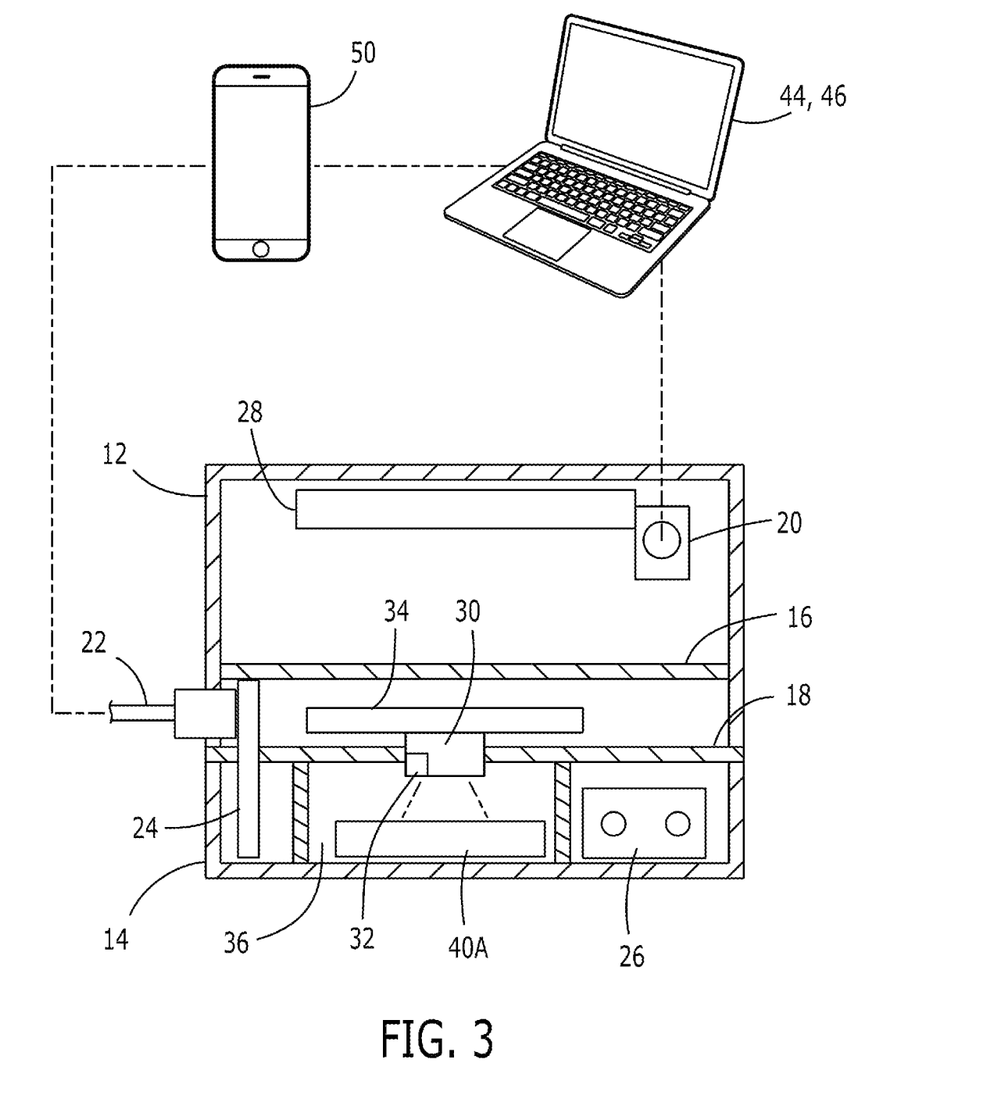
FIG. 3 conceptually illustrates a schematic view of the personal and reusable infection status passport device with parts shown in cross-section.

By way of another view, FIG. 3 conceptually illustrates a schematic view of the personal and reusable infection status passport device with parts shown in cross-section. Specifically, this figure shows the top housing enclosure 12, the bottom housing enclosure 14, the computer connection 20, the Internet connection 22, the tray insert slot 36, and the interchangeable tray 40A inserted into the tray insert slot 36.

Also shown in this figure, the personal and reusable infection status passport device 10 includes a plurality of encapsulated components comprising an upper mid shelf 16, a lower mid shelf 18, a PCB 24, a battery 26, a processor 28 (or "graphical processing unit 28"), a photosensor 30, a light source 32, and a camera photo sensor scanner 34 (referred to simply as a "scanner monitor 34"). In some embodiments, the PCB 24 comprises a processor assembled on an integrated processing board, such as without limitation, an Arduino or Raspberry Pi processor, with a wireless communication transceiver and on-board antenna. The battery 26, the photosensor 30, the PCB processor 24, wireless communication module may or may not be a single unit or individual components. The top housing enclosure 12 and the bottom housing enclosure 14 together form a device housing that encapsulates the upper mid shelf 16, the lower mid shelf 18, the PCB 24, the battery 26, the graphics processing unit 28, the photosensor 30, the light source 32, and the scanner monitor 34.

In some embodiments, a computer 44 with image processing software 46 connects to the personal and reusable infection status passport device 10 via the computer connection 20. In some embodiments, image processing will be performed onboard within the unit's PCB 24. In some embodiments, a mobile device 50 with an interactive mobile app connects to the personal and reusable infection status passport device 10 via the Internet connection 22. Alternatively, either external option of the computer 44 and the mobile device 50 may connect to the personal and reusable infection status passport device 10 via a wireless connection, such as a Bluetooth wireless connection or a WiFi wireless connection. Examples of the interactive mobile app that runs on the mobile device 50 are described next, by reference to FIGS. 4A-4D.

Figure 4A:
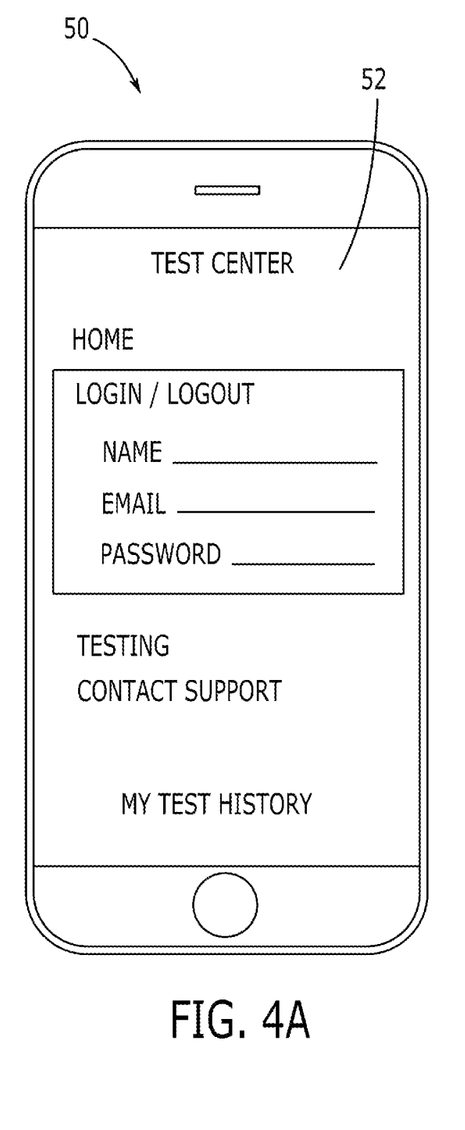
FIG. 4A conceptually illustrates an exemplary log-in screen presented in a user interface (UI) of an interactive mobile app running on a mobile device.
Figure 4B:
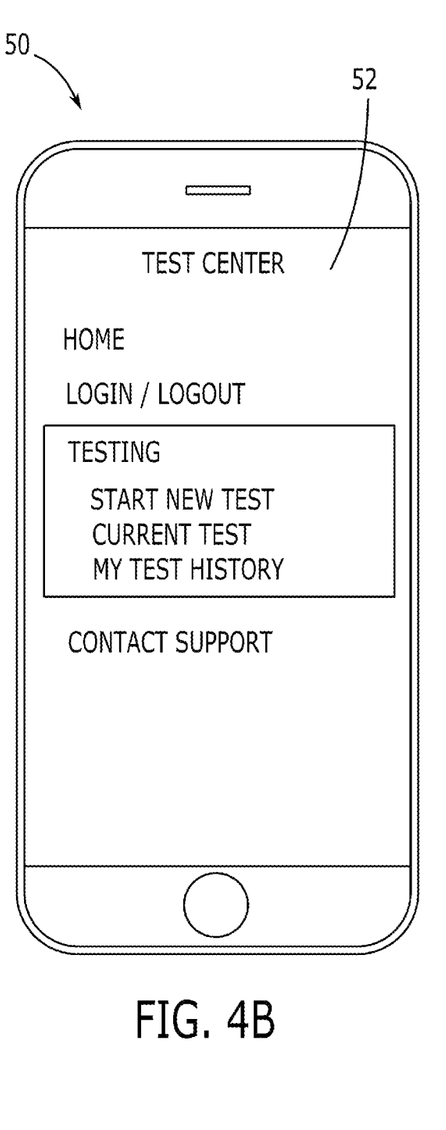
FIG. 4B conceptually illustrates an exemplary testing screen presented in the UI of the interactive mobile app running on the mobile device.
Figure 4C:
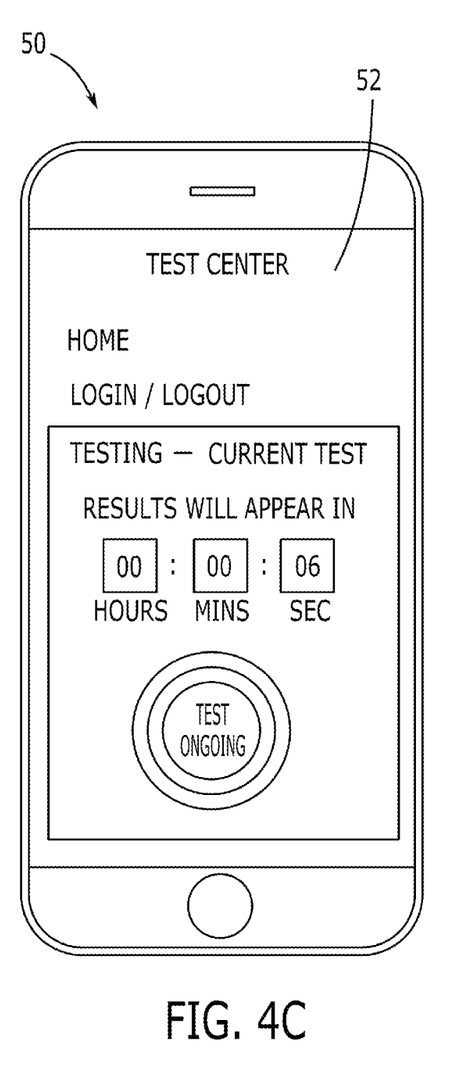
FIG. 4C conceptually illustrates an exemplary current test screen presented in the UI of the interactive mobile app running on the mobile device.
Figure 4D:
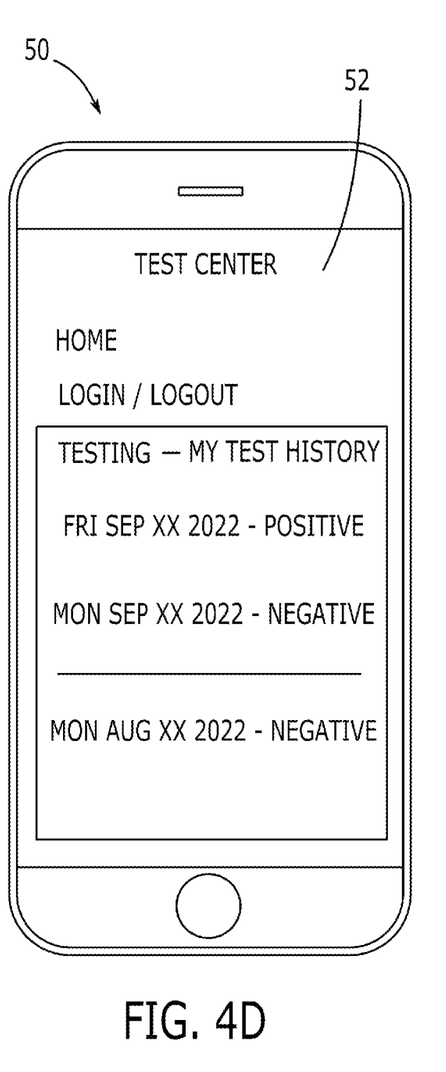
FIG. 4D conceptually illustrates an exemplary test history screen presented in the UI of the interactive mobile app running on the mobile device.

Specifically, FIG. 4A conceptually illustrates an exemplary log-in screen presented in a user interface (UI) of an interactive mobile app 52 running on the mobile device 50. FIG. 4B demonstrates an exemplary testing screen presented in the UI of the interactive mobile app 52 running on the mobile device 50. FIG. 4C conceptually illustrates an exemplary current test screen presented in the UI of the interactive mobile app 52 that is running on the mobile device 50. Finally, FIG. 4D conceptually illustrates an exemplary test history screen presented in the UI of the interactive mobile app 52 when running on the mobile device 50.

As the descriptions above reveal, the personal and reusable infection status passport device provides an easy, portable, and highly reusable solution for testing for the presence of Covid-19 other diseases or personal testing mediums. In addition to testing for Covid-19, the personal and reusable infection status passport device provides a supervisory testing unit (test tracking monitor) to ensure testing is current and accurate. That way, jurisdictional, institutional, and/or corporate entities can ensure that test results are accurate and in compliance with rules, regulations, or expectations. Furthermore, the quick and easy manner of use allows for frequent testing so the individual will know their status without spending hours at a clinic or large sums of money on many single use tests. Alternately, a company can perform testing for multiple employees as needed and can be completed quickly. Since the test strips are easy to produce, usage with the interchangeable trays provides a complete solution for most deployments. As noted above, another vital aspect of the personal and reusable infection status passport device involves the ability of Covid testing to conform to jurisdictional compliance requirements, or other such compliance requirements of government, semi-governmental agencies, non-governmental agencies, schools, corporate work, organizations, etc., the personal and reusable infection status passport device is capable of using a time stamp that ensures the test is current, not to mention invalidate tests that come from previously used test strips which had previously resulted in negative status. Moreover, the included processor and software will create a "status passport" system that will allow users to share their Covid-19 status as needed to comply with state, federal, local, OSHA, and others as needed.

Figure 5:
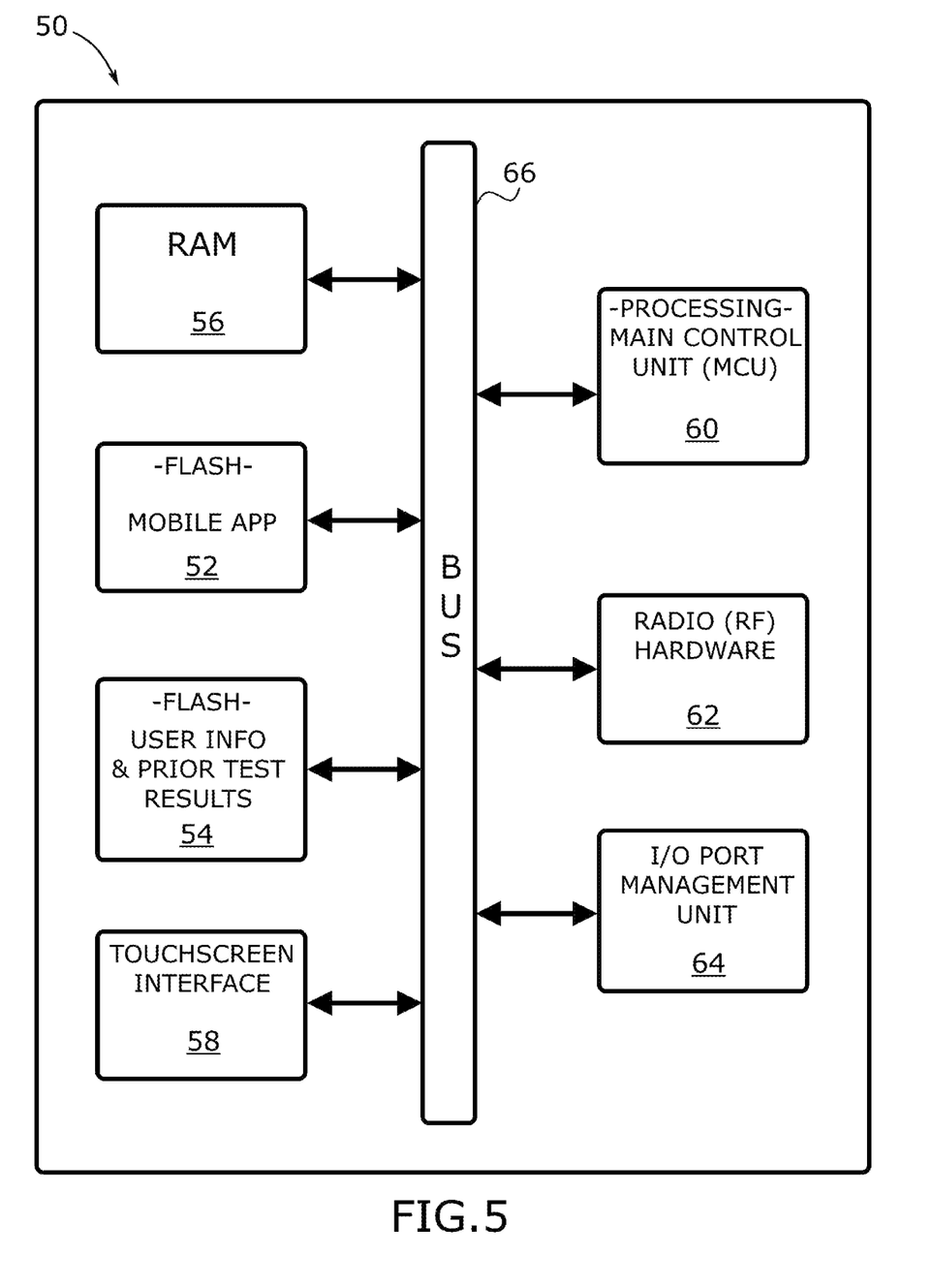
FIG. 5 conceptually illustrates electronic components of a mobile device that runs an interactive mobile application for connecting to and interacting with the personal and reusable infection status passport device to view test results by an operator of the mobile device.

Now, turning to another example, FIG. 5 conceptually illustrates electronic components of the mobile device 50 that runs an interactive mobile application for connecting to and interacting with the personal and reusable infection status passport device to view test results by an operator of the mobile device. In this example, the mobile device 50 is the mobile device noted above in reference to descriptions of FIGS. 3 and 4A-4D, or any other mobile device, such as a tablet computing device, a smartphone, etc. Specifically, the schematic view of the mobile device 50 shown in this figure illustrates several of the components that are needed to run the interactive mobile app 52 in connection with the personal and reusable infection status passport device 10. Specifically, the interactive mobile app 52 itself is installed on a first flash memory of the mobile device 50 while user information and prior test results 54 are stored in a second flash memory of the mobile device 50. In some embodiments, the user information and prior test results 54 are encrypted by way of an encryption protocol program (or code) that implements a highly secure encryption standard. Examples of highly secure encryption standards include, without limitation, SHA256, SHA512, SHA-3, etc.

The mobile device 50 shown in this figure also includes a random access memory (RAM) 56 onto which the interactive mobile app 52 and user information and prior test results 54 are loaded when connected to the personal and reusable infection status passport device 10 and/or reviewing test results after testing is completed (with or without connection to the personal and reusable infection status passport device 10). The mobile device 50 shown in this figure also includes a touchscreen display 58 onto which the user interface (UI) and different views of the interactive mobile app 52 are visually output for review and which is configured to receive user input via touch gestures.

The mobile device 50 shown in this figure also includes a mobile device process as a main control unit (MCU) 60. The MCU 60 is configured to execute instructions of the interactive mobile app 52 when loaded into RAM 56. The mobile device 50 shown in this figure also includes radio (RF) hardware 62, which may include a wireless communication transceiver, such as Bluetooth module, a WiFi module, etc. The mobile device 50 shown in this figure also includes input/output (I/O) port management unit 64 for receiving data from or transmitting data to the personal and reusable infection status passport device 10.

Finally, the mobile device 50 includes a bus 66. The bus 66 collectively represents all mobile device, peripheral device, and chipset buses that communicatively connect the numerous internal devices of the mobile device 50. For instance, the bus 66 communicatively connects the MCU 60 with the RAM 56, the flash memory units with the interactive mobile app 52 and the user info and prior test results 54, the touchscreen display 58, the RF hardware 62, and the I/O port management unit 64.

Many of the above-described features and applications are implemented as software processes that are specified as a set of instructions recorded on a computer readable storage medium (also referred to as computer readable medium, machine readable medium, or non-transitory computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor of the personal and reusable infection status passport device 10, such as the PCB 24 with processor. Also, in some embodiments, multiple software inventions can be implemented as sub-parts of a larger program while remaining distinct software inventions.

In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 6:
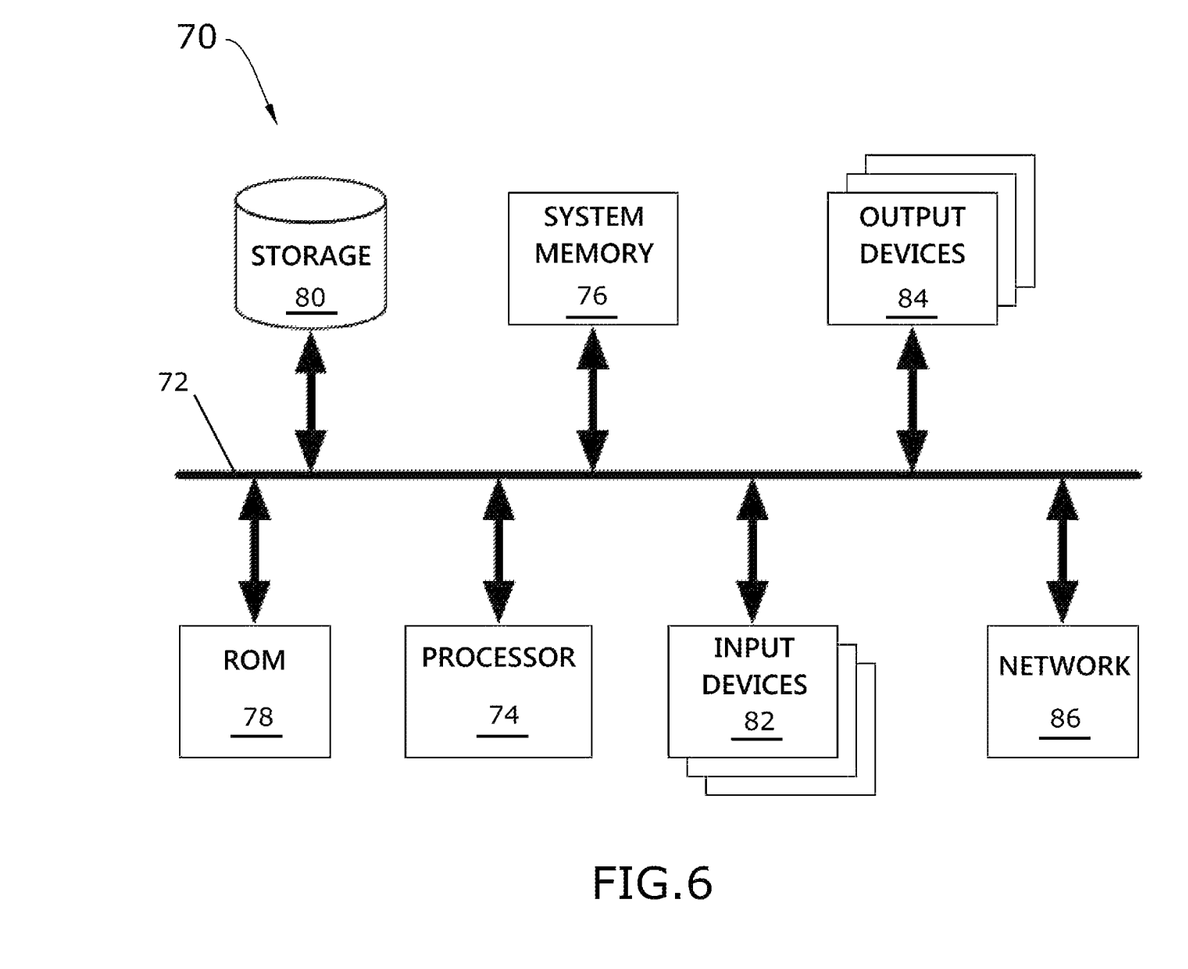
FIG. 6 conceptually illustrates an electronic system with which some embodiments of the invention are implemented.

By way of example, FIG. 6 conceptually illustrates an electronic system 70 with which some embodiments of the personal and reusable infection status passport device 10 are implemented for runtime processing of Covid-19 testing. The electronic system 70 may be a computer, such as a single board computer (e.g., Arduino) or another computing unit embedded within the personal and reusable infection status passport device 10. The electronic system 70 includes various types of computer readable media and interfaces for various other types of computer readable media. Specifically, the electronic system 70 includes a bus 72, processing unit(s) 74, a system memory 76, a read-only memory 78, a permanent storage device 80, input devices 82, output devices 84, and a network 86.

The bus 72 collectively represents all system, peripheral, and chipset buses that communicatively connect the numerous internal devices of the electronic system 70. For instance, the bus 72 communicatively connects the processing unit(s) 74 with the read-only memory 78, the system memory 76, and the permanent storage device 80.

From these various memory units, the processing unit(s) 74 retrieves instructions to execute Covid-19 testing and data to process in order to execute the processes of the invention. The processing unit(s) may be a single processor or a multi-core processor in different embodiments.

The read-only-memory (ROM) 78 stores static data and instructions that are needed by the processing unit(s) 74 and other modules of the electronic system. The permanent storage device 80, on the other hand, is a read-and-write memory device. This device is a non-volatile memory unit that stores instructions and data even when the electronic system 70 is off. Some embodiments of the invention use a mass-storage device (such as a magnetic or optical disk and its corresponding disk drive) as the permanent storage device 80.

Other embodiments use a removable storage device (such as a floppy disk or a flash drive) as the permanent storage device 80. Like the permanent storage device 80, the system memory 76 is a read-and-write memory device. However, unlike storage device 80, the system memory 76 is a volatile read-and-write memory, such as a random access memory. The system memory 76 stores some of the instructions and data that the processor needs at runtime. In some embodiments, the invention's processes are stored in the system memory 76, the permanent storage device 80, and/or the read-only memory 78. From these various memory units, the processing unit(s) 74 retrieves instructions to execute and data to process in order to execute the processes of some embodiments.

The bus 72 also connects to the input and output devices 82 and 84. The input devices enable the interchangeable trays with test strips to be input into the personal and reusable infection status passport device 10. The output devices 84 include the computer connection 20 and the Internet connection 22, and may also include other output devices, such as printers and display devices (e.g., liquid crystal displays (LCD) and organic light emitting diode (OLED) displays that are flush with the housing of the personal and reusable infection status passport device 10). Some embodiments include devices such as a touchscreen that functions as both input and output devices.

Finally, as shown in FIG. 6, bus 72 also couples electronic system 70 to a network 86 through a network adapter that includes wireless devices and modules (not shown). Such wireless devices and modules include WiFi and Bluetooth communication modules, among other wireless communication devices. In this manner, the personal and reusable infection status passport device 10 can be a part of a networked system (such as a local area network ("LAN"), a wide area network ("WAN"), or an Intranet), or a network of networks (such as the Internet).

These functions described above can be implemented in digital electronic circuitry, in computer software, firmware or hardware. The techniques can be implemented using one or more computer program products. Programmable processors and computers can be packaged or included in mobile devices (such as the interactive mobile app 52 described above, by reference to FIGS. 4A-4D). The processes and logic flows may be performed by one or more programmable processors and by sets of programmable logic circuitry. General and special purpose computing and storage devices can be interconnected through communication networks.

Some embodiments include electronic components, such as microprocessors, storage and memory that store computer program instructions in a machine-readable, computer-readable medium, or non-transitory computer readable medium. The computer-readable media may store a computer program that is executable by at least one processing unit and includes sets of instructions for performing various operations.

While the invention has been described with reference to numerous specific details, one of ordinary skill in the art will recognize that the invention can be embodied in other specific forms without departing from the spirit of the invention. For example, the personal and reusable infection status passport device 10 can be adapted for use with other viruses or illnesses. To do so, the wavelength measurements at the photosensor 30 may need to be reconfigured accordingly for the respective target virus or illness. Thus, one of ordinary skill in the art would understand that the invention is not to be limited by the foregoing illustrative details, but rather is to be defined by the appended claims.

I claim:

1. A system, comprising:
 a personal and reusable infection status passport device that is configured to test for Covid-19 or another type of infectious disease using image and color analysis, wherein the personal and reusable infection status passport device is for personal use by a user, the personal and reusable infection status passport device comprising:
  a device housing that encapsulates and secures components for the purpose of testing for a specific infectious disease comprising one of the Covid-19 or another type of infectious disease using image and color analysis;
  a single tray insert slot cut out from the housing and shaped to support a plurality of different sized designs of a plurality of different types of interchangeable trays and configured for individual insertion of each of the plurality of different types of interchangeable trays to test for the Covid-19 or another type of infectious disease,
  wherein the plurality of different types of interchangeable trays comprises a particular type of interchangeable tray comprising a particular test strip with a biosample of human bodily fluid in a discrete sample chamber prefilled with a mixed solution to test for the specific infectious disease when the particular type of interchangeable tray is inserted into the single tray insert slot with the particular test strip applied;

a clock utilized for timed testing of human biosamples provided on test strips of different types of interchangeable trays;

a light source that is configured to output light directed at a test strip of any type of interchangeable tray in the plurality of different types of interchangeable trays when the interchangeable tray is inserted into the single tray insert slot;

a photosensor that is configured to illuminate and pass light from the light source through to the particular test strip of the particular type of interchangeable tray to detect light energy associated with the specific infectious disease for the biosample, wherein the photosensor is further configured to output a signal associated with the detected light energy;

a scanner monitor that is configured to monitor, via the clock, a minimum duration of time the particular type of interchangeable tray is inserted into the single tray insert slot, wherein the scanner monitor is further configured to provide a present time stamp for the particular test strip when no prior time stamp is associated with the particular test strip, wherein the scanner monitor is further configured to output the present time stamp wherein the minimum duration of time is a required duration of time for testing the biosample of human bodily fluid for the specific infectious disease;

an on-board processor that is configured to receive the present time stamp of the particular test strip from the scanner monitor and the signal associated with the detected light energy from the photosensor, wherein the on-board processor is further configured to immediately check the particular test strip at the present time stamp for presence of one or more lines and to return a pre-used test error when at least one line is detected prior to the minimum duration of time having passed, wherein a pre-used test error is an indication that a pre-used test was inserted into the particular type of insertable tray for placement on the single tray insert slot in order to provide false results, wherein the personal and reusable infection status passport device initially checks to ensure the at least one line is not detected at the present time stamp to prevent the false results, wherein the on-board processor is further configured to analyze the signal associated with the detected light energy only if no line is initially detected for the particular test strip at the present time stamp, wherein the processor comprises the clock as an onboard clock and software to supervise a reaction to ensure a full and valid test is being performed with results that indicate whether the biosample is positive for the specific infectious disease after the minimum duration of time has passed;

a communications interface comprising a wireless communications interface, wherein the communications interface is configured to provide connectivity to an external computing device;

an on-board battery that powers the on-board processor, the clock, the light source, the photosensor, and the scanner monitor;

an interactive mobile application that is configured to display a history of prior test results for any test performed using the a personal and reusable infection status passport device, wherein the display includes a timestamp and date for each prior test result, wherein the prior test results are configured to be transmitted to the external computing device via the wireless communications interface.

2. The system of claim 1, wherein the particular type of interchangeable tray seals the particular test strip with the biosample when the particular type of interchangeable tray is inserted into the single tray insert slot to prevent exposure to moisture and dust intrusion.

3. The system of claim 1, wherein the particular test strip can be removed from the particular type of interchangeable tray to install a new test strip that is configured to fit in the particular type of interchangeable tray, wherein the new test strip includes another biosample of human bodily fluid.

4. The system of claim 1, wherein the on-board processor is configured to perform photo and color analysis on the particular test strip with the biosample of human bodily fluid.

5. The system of claim 4, wherein the on-board processor is configured to perform photo and color analysis on the particular test strip with the biosample of human bodily fluid.

6. The system of claim 1, wherein the light source is integrated into the photosensor and the scanner monitor is disposed above the photosensor.

7. The system of claim 1, wherein the detected light energy is measured in wavelengths.

8. The system of claim 1 further comprising a plurality of interface buttons and a display screen flush mounted to the device housing, wherein the display screen is configured to visually output results of the biosample test.

9. The system of claim 1, wherein the communications interface further comprises a wired communications interface.

10. The system of claim 1, wherein the software is configured to automatically run on the on-board processor to analyze the signal and display results of the biosample test, wherein the software is further configured to serve as a user interface that provides a live clock and a time since a last previous negative test result for a specific disease.

11. The system of claim 1, wherein the wireless communication interface comprises a Bluetooth wireless interface and a WiFi wireless interface.

12. The system of claim 1, wherein the mobile app is configured to transmit the results of the biosample test to an internet accessible database.

13. The system of claim 1, wherein the mobile app is further configured to start a new test for a second test strip that is inserted into a second type of interchangeable tray that is a different type of interchangeable tray than the particular type of interchangeable tray, wherein the new test starts by a user selection in the user interface (UI) to start the new test and when the second type of interchangeable tray is inserted into the single tray insert slot with the second test strip.

14. The system of claim 13, wherein the UI of the mobile app is configured to display a status of the new test while the new test is performed and visually output results of the new test after the new test is completed.

15. The system of claim 1, wherein the mobile app is tethered to a single user so that only the single user can access the personal and reusable infection status passport device at a time and the single user is required to enter user credentials to access the mobile app.

\* \* \* \* \*